(12) United States Patent
Saygili

(10) Patent No.: US 11,247,004 B2
(45) Date of Patent: Feb. 15, 2022

(54) CARTRIDGE ASSEMBLY WITH HELICOIDAL ACTIVATION

(71) Applicant: Philip Morris Products S.A., Neuchatel (CH)

(72) Inventor: Ali Murat Saygili, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 755 days.

(21) Appl. No.: 16/069,351

(22) PCT Filed: Jan. 25, 2017

(86) PCT No.: PCT/EP2017/051548
§ 371 (c)(1),
(2) Date: Jul. 11, 2018

(87) PCT Pub. No.: WO2017/129616
PCT Pub. Date: Aug. 3, 2017

(65) Prior Publication Data
US 2019/0014825 A1    Jan. 17, 2019

(30) Foreign Application Priority Data
Jan. 25, 2016  (EP) .................................... 16152639

(51) Int. Cl.
*A24F 40/42* (2020.01)
*A61M 15/06* (2006.01)
(Continued)

(52) U.S. Cl.
CPC ............ *A61M 15/06* (2013.01); *A24F 40/30* (2020.01); *A24F 40/40* (2020.01); *A24F 40/42* (2020.01);
(Continued)

(58) Field of Classification Search
CPC .............. A61M 15/06; A61M 15/0043; A24F 40/485; A24F 40/40; A24F 40/30; A24F 40/42; A24F 40/465; A24F 40/20
See application file for complete search history.

(56) References Cited

U.S. PATENT DOCUMENTS

2012/0318283 A1\* 12/2012 Watanabe ............. A61M 15/06
                                                                            131/191
2014/0182608 A1    7/2014 Egoyants et al.
(Continued)

FOREIGN PATENT DOCUMENTS

CN         102458540 A     5/2012
CN         103180053 A     6/2013
(Continued)

OTHER PUBLICATIONS

Combined Office Action and Search Report dated Jun. 28, 2020 in Chinese Patent Application No. 201780005533.0 with English translation, 11 pages.
(Continued)

*Primary Examiner* — Michael J Felton
*Assistant Examiner* — Yana B Krinker
(74) *Attorney, Agent, or Firm* — Oblon, McClelland, Maier & Neustadt, L.L.P.

(57) ABSTRACT

There is provided a cartridge assembly for an aerosol-generating system, the cartridge assembly including a cartridge, a cartridge cover, and a mouthpiece. The cartridge includes at least one compartment having an air inlet and an air outlet. The cartridge cover is helicoidally moveable with respect to the cartridge between a first position in which the air inlet is obstructed and a second position in which air may flow through the air inlet. The mouthpiece is helicoidally moveable with respect to the cartridge between a third
(Continued)

position in which the air outlet is obstructed and a fourth position in which air may flow through the air outlet.

20 Claims, 2 Drawing Sheets

(51) Int. Cl.
    *A61M 15/00*     (2006.01)
    *A24F 40/40*     (2020.01)
    *A24F 40/30*     (2020.01)
    *A24F 40/485*     (2020.01)
    *A24F 40/20*     (2020.01)
    *A24F 40/465*     (2020.01)

(52) U.S. Cl.
    CPC ....... *A24F 40/485* (2020.01); *A61M 15/0043* (2014.02); *A24F 40/20* (2020.01); *A24F 40/465* (2020.01)

(56) References Cited

U.S. PATENT DOCUMENTS

| | | | | |
|---|---|---|---|---|
| 2014/0353856 | A1* | 12/2014 | Dubief | B01F 3/04014 261/128 |
| 2015/0245661 | A1* | 9/2015 | Milin | A24F 40/40 131/329 |
| 2015/0342256 | A1* | 12/2015 | Chen | A24F 40/44 392/404 |
| 2016/0286862 | A1* | 10/2016 | Silvetrini | A24F 40/30 |

FOREIGN PATENT DOCUMENTS

| | | |
|---|---|---|
| CN | 104470388 A | 3/2015 |
| EP | 2 753 201 B1 | 2/2016 |
| JP | 5371134 B2 | 12/2013 |
| JP | 2016-523096 A | 8/2016 |
| KR | 10-2014-0110848 | 9/2014 |
| RU | 2 368 397 C2 | 4/2009 |
| WO | WO 2008/121610 A1 | 10/2008 |
| WO | WO 2015/000974 A1 | 1/2015 |
| WO | WO 2015/197627 A1 | 12/2015 |
| WO | WO 2017/032695 A1 | 3/2017 |
| WO | WO 2017/108983 A1 | 6/2017 |

OTHER PUBLICATIONS

Notice of Allowance dated Jun. 11, 2020 in Russian Patent Application No. 2018130374 (with English translation), 17 pages.
Russian Search Report dated Jun. 11, 2020 in Russian Patent Application No. 2018130374 (with English translation), 4 pages.
Decision to Grant a Patent dated Jan. 21, 2021 in Japanese Patent Application No. 2018-536438 (with English language translation), 5 pages.
International Search Report and Written Opinion dated May 4, 2017, in PCT/EP2017/051548 filed Jan. 25, 2017.

\* cited by examiner

CARTRIDGE ASSEMBLY WITH HELICOIDAL ACTIVATION

The present invention relates to a cartridge assembly for use in an aerosol-generating system and an aerosol-generating system comprising the cartridge assembly. The present invention finds particular application as a cartridge assembly comprising a nicotine source and an acid source for the generation of an aerosol comprising nicotine salt particles.

Devices for delivering nicotine to a user and comprising a nicotine source and a volatile delivery enhancing compound source are known. For example, WO 2008/121610 A1 discloses devices in which nicotine and a volatile acid, such as pyruvic acid, are reacted with one another in the gas phase to form an aerosol of nicotine salt particles that is inhaled by the user.

In WO 2008/121610 A1 the nicotine source and volatile delivery enhancing compound source may be housed in compartments that are sealed by one or more removable or frangible barriers prior to initial use of the aerosol-generating system.

However, the inclusion of one or more removable or frangible barriers may disadvantageously increase the cost and complexity of manufacturing such aerosol-generating systems. Consequently, it would be desirable to provide a cartridge assembly for use in an aerosol-generating system in which one or more volatile compounds may be retained during storage without the use of removable or frangible barriers.

According to a first aspect of the present invention there is provided a cartridge assembly for use in an aerosol-generating system, the cartridge assembly comprising a cartridge, a mouthpiece and a cartridge cover. The cartridge comprises at least one compartment having an air inlet and an air outlet, and at least one cartridge actuation portion on an outer surface of the cartridge. The mouthpiece comprises a mouthpiece cavity, wherein a downstream end of the cartridge is received within the mouthpiece cavity. The mouthpiece further comprises a mouthpiece wall portion extending across a downstream end of the mouthpiece cavity, the mouthpiece wall portion comprising a mouthpiece air inlet. The mouthpiece also comprises a mouthpiece actuation portion on an inner surface of the mouthpiece cavity and engaged with the at least one cartridge actuation portion. The cartridge cover comprises a cartridge cover cavity, wherein an upstream end of the cartridge is received within the cartridge cover cavity. The cartridge cover further comprises a cartridge cover wall portion extending across an upstream end of the cartridge cover cavity, the cartridge cover wall portion comprising a cartridge cover air inlet. The cartridge cover also comprises a cartridge cover actuation portion on an inner surface of the cartridge cover cavity and engaged with the at least one cartridge actuation portion. The at least one cartridge actuation portion and the cartridge cover actuation portion are configured so that the cartridge cover is helicoidally moveable with respect to the cartridge from a first position in which the cartridge cover wall portion abuts an upstream end of the cartridge and obstructs the air inlet of the at least one compartment, to a second position in which the cartridge cover wall portion is spaced apart from the upstream end of the cartridge and the cartridge cover air inlet is in fluid communication with the air inlet of the at least one compartment. The at least one cartridge actuation portion and the mouthpiece actuation portion are configured so that the mouthpiece is helicoidally moveable with respect to the cartridge from a third position in which the mouthpiece wall portion abuts a downstream end of the cartridge and obstructs the air outlet of the at least one compartment, to a fourth position in which the mouthpiece wall portion is spaced apart from the downstream end of the cartridge and the mouthpiece air inlet is in fluid communication with the air outlet of the at least one compartment.

As used herein with reference to the invention, the term "air inlet" is used to describe one or more apertures through which air may be drawn into a component or portion of a component of the cartridge assembly.

As used herein with reference to the invention, the term "air outlet" is used to describe one or more apertures through which air may be drawn out of a component or portion of a component of the cartridge assembly.

As used herein with reference to the invention, by "obstructed" it is meant that an air inlet or an air outlet is blocked such that airflow through the air inlet or the air outlet is substantially prevented.

Advantageously, a cartridge assembly according to the present invention minimises or substantially prevents the loss of one or more volatile compounds stored within the cartridge assembly before the cartridge assembly is used in an aerosol-generating system. Specifically, the obstruction of the air inlet of the at least one compartment of the cartridge by the cartridge cover wall portion when the cartridge cover is in the first position, and the obstruction of the air outlet of the at least one compartment of the cartridge by the mouthpiece wall portion when the mouthpiece is in the third position, may minimise or substantially prevent the loss of one or more volatile compounds stored within the cartridge.

Advantageously, by using a cartridge cover and a mouthpiece that are both helicoidally moveable with respect to a cartridge, a cartridge assembly according to the present invention can eliminate the need to use one or more removable or frangible barriers to seal the cartridge.

Advantageously, a cartridge assembly according to the present invention provides a reliable, consistent and simple means for activating the cartridge. Specifically, the cartridge assembly being configured so that turning the cartridge cover and the mouthpiece with respect to the cartridge to uncover the air inlet and the air outlet of the at least one compartment of the cartridge minimises the risk of user error when activating the cartridge.

The cartridge cover actuation portion may comprise a first helical guide slot and the at least one cartridge actuation portion may comprise a first projection positioned within the first helical guide slot. The mouthpiece actuation portion may comprise a second helical guide slot and the at least one cartridge actuation portion may comprise a second projection positioned within the second helical guide slot. Using a combination of helical guide slot and a projection may provide a simple means for effecting the helicoidal motion between the cartridge and one or both of the cartridge cover and the mouthpiece. A helicoidal guide slot may transform a rotational force into a helicoidal motion. For example, providing first and second helical guide slots and first and second projections may transform a rotational movement of the cartridge cover with respect to the mouthpiece into a helicoidal movement of each of the cartridge cover and the mouthpiece with respect to the cartridge.

Preferably, the first projection engages a first end of the first helical guide slot when the cartridge cover is in the second position, the engagement between the first projection and the first end of the first helical guide slot preventing further helicoidal movement of the cartridge cover with respect to the cartridge in a direction away from the first position. Advantageously, limiting movement of the cartridge cover with respect to the cartridge in a direction away from the first position eliminates the need for a user to grasp the cartridge when activating the cartridge assembly. Without limiting movement of the cartridge cover with respect to the cartridge, it may be necessary for a user to hold the cartridge stationary while separately turning each of the cartridge cover and the mouthpiece with respect to the cartridge. In embodiments in which a first end of the first helical guide slot limits movement of the cartridge cover with respect to the cartridge, the user may activate the cartridge by grasping and turning only the cartridge cover and the mouthpiece with respect to each other. For example, by grasping and turning the mouthpiece and the cartridge cover with respect to each other, the user may turn the cartridge cover through a helicoidal motion with respect to the cartridge from the first position until the cartridge cover reaches the second position, at which point the first projection engages the first end of the first helical guide slot. At this point, by further turning the cartridge cover and the mouthpiece with respect to each other, the engagement between the first projection and the first end of the first helical guide slot will transfer the turning force from the cartridge cover to the cartridge so that the cartridge and the mouthpiece turn through a helicoidal motion with respect to each other until the mouthpiece moves from the third position to the fourth position.

Preferably, the second projection engages a first end of the second helical guide slot when the mouthpiece is in the fourth position, the engagement between the second projection and the first end of the second helical guide slot preventing further helicoidal movement of the mouthpiece with respect to the cartridge in a direction away from the third position. Advantageously, limiting movement of the mouthpiece with respect to the cartridge in a direction away from the third position eliminates the need for a user to grasp the cartridge when activating the cartridge assembly. Without limiting movement of the mouthpiece with respect to the cartridge, and in those embodiments in which the first projection does not engage a first end of the first helical guide slot when the cartridge cover is in the second position, it may be necessary for a user to hold the cartridge stationary while separately turning each of the cartridge cover and the mouthpiece with respect to the cartridge. In embodiments in which a first end of the second helical guide slot limits movement of the mouthpiece with respect to the cartridge, the user may activate the cartridge by grasping and turning only the cartridge cover and the mouthpiece with respect to each other. For example, by grasping and turning the mouthpiece and the cartridge cover with respect to each other, the user may turn the mouthpiece through a helicoidal motion with respect to the cartridge from the third position until the mouthpiece reaches the fourth position, at which point the second projection engages the first end of the second helical guide slot. At this point, by further turning the cartridge cover and the mouthpiece with respect to each other, the engagement between the second projection and the first end of the second helical guide slot will transfer the turning force from the mouthpiece to the cartridge so that the cartridge and the cartridge cover turn through a helicoidal motion with respect to each other until the cartridge cover moves from the first position to the second position.

The cartridge assembly may be configured so that the first and second projections engage first ends of the first and second helical guide slots, respectively, when the cartridge cover and the mouthpiece are in the second and fourth positions. In addition to enabling a user to activate the cartridge assembly by grasping and turning only the cartridge cover and the mouthpiece, as described herein, such a configuration may limit the range of helicoidal motion of the cartridge cover and the mouthpiece with respect to the cartridge. Limiting the range of helicoidal motion of the cartridge cover and the mouthpiece with respect to the cartridge may prevent excessive turning of the cartridge cover and the mouthpiece by a user, which may damage the cartridge assembly.

The at least one cartridge actuation portion may comprise a first helical thread, wherein the cartridge cover actuation portion comprises a second helical thread engaged with an upstream end of the first helical thread, and wherein the mouthpiece actuation portion comprises a third helical thread engaged with a downstream end of the first helical thread.

Preferably, the cartridge cover comprises a first mechanical stop and the cartridge comprises a second mechanical stop, wherein the first mechanical stop engages the second mechanical stop when the cartridge cover is in the second position. The engagement between the first and second mechanical stops preferably prevents further helicoidal movement of the cartridge cover with respect to the cartridge in a direction away from the first position. Advantageously, providing first and second mechanical stops eliminates the need for a user to grasp the cartridge when activating the cartridge assembly. Without first and second mechanical stops, it may be necessary for a user to hold the cartridge stationary while separately turning each of the cartridge cover and the mouthpiece with respect to the cartridge. In embodiments in which the cartridge assembly comprises first and second mechanical stops, the user may activate the cartridge by grasping and turning only the cartridge cover and the mouthpiece with respect to each other. For example, by grasping and turning the mouthpiece and the cartridge cover with respect to each other, the user may turn the cartridge cover through a helicoidal motion with respect to the cartridge from the first position until the cartridge cover reaches the second position, at which point the first mechanical stop engages the second mechanical stop. At this point, by further turning the cartridge cover and the mouthpiece with respect to each other, the engagement between the first and second mechanical stops will transfer the turning force from the cartridge cover to the cartridge so that the cartridge and the mouthpiece turn through a helicoidal motion with respect to each other until the mouthpiece moves from the third position to the fourth position.

The mouthpiece may comprise a third mechanical stop and the cartridge may comprise a fourth mechanical stop, wherein the third mechanical stop engages the fourth mechanical stop when the mouthpiece is in the fourth position. Preferably, the engagement between the third and fourth mechanical stops prevents further helicoidal movement of the mouthpiece with respect to the cartridge in a direction away from the third position. Advantageously, providing third and fourth mechanical stops eliminates the need for a user to grasp the cartridge when activating the cartridge assembly. Without third and fourth mechanical stops, and in those embodiments without first and second mechanical stops, it may be necessary for a user to hold the cartridge stationary while separately turning each of the cartridge cover and the mouthpiece with respect to the cartridge. In embodiments in which the cartridge assembly comprises third and fourth mechanical stops, the user may activate the cartridge by grasping and turning only the cartridge cover and the mouthpiece with respect to each other. For example, by grasping and turning the mouthpiece and the cartridge cover with respect to each other, the user may turn the mouthpiece through a helicoidal motion with respect to the cartridge from the third position until the mouthpiece reaches the fourth position, at which point the third mechanical stop engages the fourth mechanical stop. At this point, by further turning the cartridge cover and the mouthpiece with respect to each other, the engagement between the third and fourth mechanical stops will transfer the turning force from the mouthpiece to the cartridge so that the cartridge and the cartridge cover turn through a helicoidal motion with respect to each other until the cartridge cover moves from the first position to the second position.

The cartridge assembly may comprise first, second, third and fourth mechanical stops. In addition to enabling a user to activate the cartridge assembly by grasping and turning only the cartridge cover and the mouthpiece, as described herein, providing first, second, third and fourth mechanical may limit the range of helicoidal motion of the cartridge cover and the mouthpiece with respect to the cartridge. Limiting the range of helicoidal motion of the cartridge cover and the mouthpiece with respect to the cartridge may prevent excessive turning of the cartridge cover and the mouthpiece by a user, which may damage the cartridge assembly.

Preferably, the cartridge assembly is configured to define the second position of the cartridge cover at an angular rotation with respect to the cartridge of between about 70 degrees and about 110 degrees from the first position. Configuring the cartridge assembly for an angular rotation between the first and second positions within this range may advantageously provide sufficient separation between the cartridge cover wall portion and the cartridge so that sufficient airflow is achieved through the air inlet of the at least one compartment of the cartridge when the cartridge cover is in the second position. Configuring the cartridge assembly for an angular rotation between the first and second positions within this range may advantageously facilitate turning of the cartridge cover by a user from the first position to the second position in a single motion.

Preferably, the cartridge assembly is configured to define the fourth position of the mouthpiece at an angular rotation with respect to the cartridge of between about 70 degrees and about 110 degrees from the third position. Configuring the cartridge assembly for an angular rotation between the third and fourth positions within this range may advantageously provide sufficient separation between the mouthpiece wall portion and the cartridge so that sufficient airflow is achieved through the air outlet of the at least one compartment of the cartridge when the mouthpiece is in the fourth position. Configuring the cartridge assembly for an angular rotation between the third and fourth positions within this range may advantageously facilitate turning of the mouthpiece by a user from the third position to the fourth position in a single motion.

Each of the cartridge cover and the mouthpiece is preferably configured for two-way helicoidal movement with respect to the cartridge so that the cartridge cover is moveable from the second position to the first position and the mouthpiece is moveable from the fourth position to the third position. Advantageously, such a cartridge assembly provides a reliable and consistent means for deactivating the cartridge. That is, turning the cartridge cover into the first position and the mouthpiece into the third position re-obstructs the air inlet and the air outlet of the at least one compartment of the cartridge with the cartridge cover wall portion and the mouthpiece wall portion respectively. This advantageously minimises or substantially prevents loss of any remaining volatile compounds stored within the cartridge when the cartridge assembly is not in use.

Therefore, such a cartridge assembly may advantageously eliminate the need for a user to consume the entire volatile contents of the cartridge in a single experience, as the cartridge assembly can be deactivated after each use.

The mouthpiece may comprise a mouthpiece chamber positioned downstream of the mouthpiece wall portion, wherein the mouthpiece air inlet is in fluid communication with the mouthpiece chamber, and wherein the mouthpiece further comprises a mouthpiece air outlet at a downstream end of the mouthpiece chamber. Providing a mouthpiece chamber positioned downstream of the mouthpiece wall portion may be advantageous in embodiments in which a plurality of volatile reactants are stored separately within the cartridge. That is, the volatile reactants may be reacted in the gas phase within the mouthpiece chamber before the reaction product is delivered to a user through the mouthpiece air outlet.

The mouthpiece may comprise a ventilation air inlet providing fluid communication between the exterior of the mouthpiece and the mouthpiece chamber, wherein the ventilation air inlet is positioned between the mouthpiece wall portion and the downstream end of the mouthpiece chamber.

The at least one compartment may comprise a first compartment having a first air inlet and a first air outlet and a second compartment having a second air inlet and a second air outlet. Such an embodiment may be particularly advantageous when it is desirable to separately store first and second volatile compounds within the cartridge. That is, a first volatile compound may be stored within the first compartment and a second volatile compound may be stored within the second compartment.

When the cartridge cover is in the first position, preferably the cartridge cover wall portion obstructs the first air inlet and the second air inlet of the first and second compartments on the cartridge. When the mouthpiece is in the third position, preferably the mouthpiece wall portion obstructs the first air outlet and the second air outlet of the first and second compartments on the cartridge.

The cartridge cover air inlet may comprise a single air inlet. In embodiments in which the cartridge comprises first and second air inlets of first and second compartment, preferably the cartridge cover air inlet comprises a third air inlet and a fourth air inlet, wherein the third air inlet is aligned with the first air inlet and the fourth air inlet is aligned with the second air inlet when the cartridge cover is in the second position.

In embodiments in which the cartridge comprises first and second compartments, the cartridge may comprise a nicotine source positioned within the first compartment and an acid source positioned within the second compartment.

As used herein with reference to the invention, the term "nicotine", is used to describe nicotine, nicotine base or a nicotine salt.

The nicotine source may comprise a first carrier material impregnated with between about 1 milligram and about 50 milligrams of nicotine. The nicotine source may comprise a first carrier material impregnated with between about 1 milligram and about 40 milligrams of nicotine. Preferably, the nicotine source comprises a first carrier material impregnated with between about 3 milligrams and about 30 milligrams of nicotine. More preferably, the nicotine source comprises a first carrier material impregnated with between about 6 milligrams and about 20 milligrams of nicotine. Most preferably, the nicotine source comprises a first carrier material impregnated with between about 8 milligrams and about 18 milligrams of nicotine.

In embodiments in which the first carrier material is impregnated with nicotine base or a nicotine salt, the amounts of nicotine recited herein are the amount of nicotine base or amount of ionised nicotine, respectively.

The first carrier material may be impregnated with liquid nicotine or a solution of nicotine in an aqueous or non-aqueous solvent.

The first carrier material may be impregnated with natural nicotine or synthetic nicotine. The acid source may comprise an organic acid or an inorganic acid.

Preferably, the acid source comprises an organic acid, more preferably a carboxylic acid, most preferably an alpha-keto or 2-oxo acid or lactic acid.

Advantageously, the acid source comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid, lactic acid and combinations thereof. Advantageously, the acid source comprises pyruvic acid or lactic acid. More advantageously, the acid source comprises lactic acid.

Advantageously, the acid source comprises a second carrier material impregnated with acid.

The first carrier material and the second carrier material may be the same or different. Advantageously, the first carrier material and the second carrier material have a density of between about 0.1 grams/cubic centimetre and about 0.3 grams/cubic centimetre.

Advantageously, the first carrier material and the second carrier material have a porosity of between about 15 percent and about 55 percent.

The first carrier material and the second carrier material may comprise one or more of glass, cellulose, ceramic, stainless steel, aluminium, polyethylene (PE), polypropylene, polyethylene terephthalate (PET), poly(cyclohexanedimethylene terephthalate) (PCT), polybutylene terephthalate (PBT), polytetrafluoroethylene (PTFE), expanded polytetrafluoroethylene (ePTFE), and BAREX®.

The first carrier material acts as a reservoir for the nicotine.

Advantageously, the first carrier material is chemically inert with respect to nicotine.

The first carrier material may have any suitable shape and size. For example, the first carrier material may be in the form of a sheet or plug.

Advantageously, the shape and size of the first carrier material is similar to the shape and size of the first compartment of the cartridge.

The shape, size, density and porosity of the first carrier material may be chosen to allow the first carrier material to be impregnated with a desired amount of nicotine.

Advantageously, the first compartment of the cartridge may further comprise a flavourant. Suitable flavourants include, but are not limited to, menthol.

Advantageously, the first carrier material may be impregnated with between about 3 milligrams and about 12 milligrams of flavourant.

The second carrier material acts as a reservoir for the acid.

Advantageously, the second carrier material is chemically inert with respect to the acid.

The second carrier material may have any suitable shape and size. For example, the second carrier material may be in the form of a sheet or plug.

Advantageously, the shape and size of the second carrier material is similar to the shape and size of the second compartment of the cartridge.

The shape, size, density and porosity of the second carrier material may be chosen to allow the second carrier material to be impregnated with a desired amount of acid.

Advantageously, acid source is a lactic acid source comprising a second carrier material impregnated with between about 2 milligrams and about 60 milligrams of lactic acid.

Preferably, the lactic acid source comprises a second carrier material impregnated with between about 5 milligrams and about 50 milligrams of lactic acid. More preferably, the lactic acid source comprises a second carrier material impregnated with between about 8 milligrams and about 40 milligrams of lactic acid. Most preferably, the lactic acid source comprises a second carrier material impregnated with between about 10 milligrams and about 30 milligrams of lactic acid.

The shape and dimensions of the first compartment of the cartridge may be chosen to allow a desired amount of nicotine to be housed in the cartridge.

The shape and dimensions of the second compartment of the cartridge may be chosen to allow a desired amount of acid to be housed in the cartridge.

The ratio of nicotine and acid required to achieve an appropriate reaction stoichiometry may be controlled and balanced through variation of the volume of the first compartment relative to the volume of the second compartment.

The first air inlet of the first compartment of the cartridge and the second air inlet of the second compartment of the cartridge may each comprise one or more apertures. For example, the first air inlet of the first compartment of the cartridge and the second air inlet of the second compartment of the cartridge may each comprise one, two, three, four, five, six or seven apertures.

The first air inlet of the first compartment of the cartridge and the second air inlet of the second compartment of the cartridge may comprise the same or different numbers of apertures.

Advantageously, the first air inlet of the first compartment of the cartridge and the second air inlet of the second compartment of the cartridge each comprise a plurality of apertures. For example, the first air inlet of the first compartment of the cartridge and the second air inlet of the second compartment of the cartridge may each comprise two, three, four, five, six or seven apertures.

Providing a first compartment having a first air inlet comprising a plurality of apertures and a second compartment having a second air inlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air inlet of the first compartment of the cartridge relative to the number, dimensions and location of the apertures forming the second air inlet of the second compartment of the cartridge.

In embodiments in which the acid source comprises lactic acid, advantageously the flow area of the second air inlet of the second compartment of the cartridge is greater than the flow area of the first air inlet of the first compartment of the cartridge.

As used herein with reference to the invention, the term "flow area" is used to describe the cross-sectional area of an air inlet or air outlet through which airflows during use. In embodiments in which an air inlet or air outlet comprises a plurality of apertures, the flow area of the air inlet or air outlet is the total flow area of the air inlet or air outlet and is equal to the sum of the flow areas of each of the plurality of apertures forming the air inlet or air outlet. In embodiments in which the cross-sectional area of an air inlet or air outlet varies in the direction of airflow, the flow area of the air inlet or air outlet is the minimum cross-sectional area in the direction of airflow.

Increasing the flow area of the second air inlet of the second compartment of the cartridge relative to the flow area of the first air inlet of the first compartment of the cartridge advantageously increases the volumetric airflow through the second air inlet compared to the volumetric airflow through the first air inlet.

In embodiments in which the acid source comprises lactic acid, preferably the ratio of the flow area of the first air inlet of the first compartment of the cartridge to the flow area of the second air inlet of the second compartment of the cartridge is between about 3:4 and about 1:2. More preferably, the ratio of the flow area of the first air inlet of the first compartment of the cartridge to the flow area of the second air inlet of the second compartment of the cartridge is between about 2:3 and about 1:2.

The flow area of the second air inlet of the second compartment of the cartridge may be increased relative to the flow area of the first air inlet of the first compartment of the cartridge by one or both of increasing the size of the one or more apertures forming the second air inlet relative to the size of the one or more apertures forming the first air inlet and increasing the number of apertures forming the second air inlet relative to the number of apertures forming the first air inlet.

Advantageously, the flow area of the second air inlet of the second compartment of the cartridge is increased relative to the flow area of the first air inlet of the first compartment of the cartridge by increasing the number of apertures forming the second air inlet relative to the number of apertures forming the first air inlet.

Advantageously, the first air inlet of the first compartment of the cartridge comprises between 2 and 5 apertures.

Advantageously, the second air inlet of the second compartment of the cartridge comprises between 3 and 7 apertures.

Advantageously, the flow area of the first air inlet of the first compartment of the cartridge is between about 0.1 square millimetres and about 1.6 square millimetres, more advantageously between about 0.2 square millimetres and about 0.8 square millimetres.

In embodiments in which the first air inlet of the first compartment of the cartridge comprises a plurality of apertures, the apertures may have different flow areas so that the flow area of the first air inlet of the first compartment of the cartridge is divided unequally between the apertures forming the first air inlet.

In embodiments in which the first air inlet of the first compartment of the cartridge comprises a plurality of apertures, each of the apertures may have the same flow area so that the flow area of the first air inlet of the first compartment of the cartridge is divided equally between the apertures forming the first air inlet. Providing a first compartment having a first air inlet comprising a plurality of apertures having substantially the same flow area may advantageously simplify manufacturing of the cartridge.

The first air inlet of the first compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

In embodiments in which the acid source comprises lactic acid, advantageously the flow area of the second air inlet of the second compartment of the cartridge is between about 0.2 square millimetres and about 2.4 square millimetres, more advantageously between about 0.4 square millimetres and about 1.2 square millimetres.

In embodiments in which the second air inlet of the second compartment of the cartridge comprises a plurality of apertures, the apertures may have different flow areas so that the total flow area of the second air inlet of the second compartment of the cartridge is divided unequally between the apertures forming the second air inlet.

In embodiments in which the second air inlet of the second compartment of the cartridge comprises a plurality of apertures, each of the apertures may have the same flow area so that the total flow area of the second air inlet of the second compartment of the cartridge is divided equally between the apertures forming the second air inlet. Providing a second compartment having a second air inlet comprising a plurality of apertures having substantially the same flow area may advantageously simplify manufacturing of the cartridge.

The second air inlet of the second compartment of the cartridge may comprise one or more apertures having any suitable cross-sectional shape. For example, the cross-sectional shape of each aperture may be circular, elliptical, square or rectangular. Advantageously, each aperture has a substantially circular cross-sectional shape. Advantageously, the diameter of each aperture is between about 0.2 millimetres and about 0.6 millimetres.

The first air outlet of the first compartment of the cartridge and the second air outlet of the second compartment of the cartridge may each comprise one or more apertures. For example, the first air outlet of the first compartment of the cartridge and the second air outlet of the second compartment of the cartridge may each comprise one, two, three, four, five, six or seven apertures.

The first air outlet of the first compartment of the cartridge and the second air outlet of the second compartment of the cartridge may comprise the same or different numbers of apertures.

Advantageously, the first air outlet of the first compartment of the cartridge and the second air outlet of the second compartment of the cartridge may each comprise a plurality of apertures. For example, the first air outlet of the first compartment of the cartridge and the second air outlet of the second compartment of the cartridge may each comprise two, three, four, five, six or seven apertures. Providing a first compartment having a first air outlet comprising a plurality of apertures and a second compartment having a second air outlet comprising a plurality of apertures may advantageously result in more homogeneous airflow within the first compartment and the second compartment, respectively. In use, this may improve entrainment of nicotine in an air stream drawn through the first compartment and improve entrainment of acid in an air stream drawn through the second compartment.

In embodiments in which the first air outlet of the first compartment of the cartridge comprises a plurality of apertures, advantageously the first air outlet comprises between 2 and 5 apertures.

In embodiments in which the second air outlet of the second compartment of the cartridge comprises a plurality of apertures, advantageously, the second air outlet comprises between 3 and 7 apertures.

Advantageously, the first air outlet of the first compartment of the cartridge and the second air outlet of the second compartment of the cartridge may each comprise a single aperture. Providing a first compartment having a first air outlet comprising a single aperture and a second compartment having a second air outlet comprising a single aperture may advantageously simplify manufacturing of the cartridge.

The ratio of nicotine and acid required to achieve an appropriate reaction stoichiometry may be controlled and balanced through variation of the volumetric airflow through the first compartment of the cartridge relative to the volumetric airflow through the second compartment of the cartridge. The ratio of the volumetric airflow through the first compartment relative to the volumetric airflow through the second compartment may be controlled through variation of one or more of the number, dimensions and location of the apertures forming the first air outlet of the first compartment of the cartridge relative to the number, dimensions and location of the apertures forming the second air outlet of the second compartment of the cartridge.

The flow area of the first air outlet of the first compartment may be the same as or different to the flow area of the second air outlet of the second compartment.

The flow area of the second air outlet of the second compartment of the cartridge may be greater than flow area of the first air outlet of the first compartment of the cartridge. Increasing the flow area of the second air outlet of the second compartment of the cartridge relative to the flow area of the first air outlet of the first compartment of the cartridge may advantageously increase the volumetric airflow through the second air outlet compared to the volumetric airflow through the first air outlet.

In embodiments in which the acid source comprises lactic acid, the ratio of the flow area of the first air outlet of the first compartment of the cartridge to the flow area of the second air outlet of the second compartment of the cartridge is preferably between about 3:4 and about 1:2. More preferably, the ratio of the flow area of the first air outlet of the first compartment of the cartridge to the flow area of the second air outlet of the second compartment of the cartridge is between about 2:3 and about 1:2.

In embodiments in which the flow area of the second air outlet of the second compartment of the cartridge is greater than flow area of the first air outlet of the first compartment of the cartridge, the flow area of the second air outlet of the second compartment of the cartridge may be increased relative to the flow area of the first air outlet of the first compartment of the cartridge by one or both of increasing the size of the one or more apertures forming the second air outlet relative to the size of the one or more apertures forming the first air outlet and increasing the number of apertures forming the second air outlet relative to the number of apertures forming the first air outlet.

Advantageously, the flow area of the second air outlet of the second compartment of the cartridge is increased relative to the flow area of the first air outlet of the first compartment of the cartridge by increasing the number of apertures forming the second air outlet relative to the number of apertures forming the first air outlet.

The first air inlet and the first air outlet of the first compartment of the cartridge may comprise the same or different numbers of apertures.

Advantageously, the first air inlet and the first air outlet of the first compartment of the cartridge comprise the same numbers of apertures. Providing a first compartment having a first air inlet and a first air outlet comprising the same number of apertures may advantageously simplify manufacturing of the cartridge.

The second air inlet and the second air outlet of the second compartment of the cartridge may comprise the same or different numbers of apertures.

Advantageously, the second air inlet and the second air outlet of the second compartment of the cartridge comprise the same numbers of apertures. Providing a second compartment having a second air inlet and a second air outlet comprising the same number of apertures may advantageously simplify manufacturing of the cartridge.

Advantageously, the flow area of the first air outlet of the first compartment of the cartridge is between about 0.1 square millimetres and about 5 square millimetres.

In embodiments in which the first air outlet of the first compartment of the cartridge comprises a plurality of apertures, the apertures may have different flow areas so that the flow area of the first air outlet of the first compartment of the cartridge is divided unequally between the apertures forming the first air outlet.

In embodiments in which the first air outlet of the first compartment of the cartridge comprises a plurality of apertures, each of the apertures may have the same flow area so that the flow area of the first air outlet of the first compartment of the cartridge is divided equally between the apertures forming the first air outlet. Providing a first compartment having a first air outlet comprising a plurality of apertures having substantially the same flow area may advantageously simplify manufacturing of the cartridge.

The first air outlet of the first compartment of the cartridge may comprise one or more apertures having any suitable cross-sectional shape. For example, the cross-sectional shape of each aperture may be circular, elliptical, square or rectangular. In embodiments in which the first air outlet of the first compartment of the cartridge comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the first air inlet of the first compartment of the cartridge may be the same as or different to the dimensions of the one or more apertures forming the first air outlet of the first compartment of the cartridge.

Advantageously, the dimensions of the one or more apertures forming the first air inlet of the first compartment of the cartridge may be substantially the same as the dimensions of the one or more apertures forming the first air outlet of the first compartment of the cartridge. Providing a first compartment having a first air inlet and a first air outlet comprising one or more apertures of substantially the same dimensions may advantageously simplify manufacturing of the cartridge.

Advantageously, the dimensions of the one or more apertures forming the first air outlet of the first compartment of the cartridge may be greater than the dimensions of the one or more apertures forming the first air inlet of the first compartment of the cartridge. Increasing the dimensions of the apertures forming the first air outlet of the first compartment of the cartridge relative to the dimensions of the apertures forming the first air inlet of the first compartment of the cartridge may advantageously reduce the risk of the first air outlet of the first compartment of the cartridge becoming obstructed by, for example, dust.

Advantageously, the flow area of the second air outlet of the second compartment of the cartridge is between about 0.1 square millimetres and about 5 square millimetres.

In embodiments in which the second air outlet of the second compartment of the cartridge comprises a plurality of apertures, the apertures may have different flow areas so that the total flow area of the second air outlet of the second compartment of the cartridge is divided unequally between the apertures forming the second air outlet.

In embodiments in which the second air outlet of the second compartment of the cartridge comprises a plurality of apertures, each of the apertures may have the same flow area so that the total flow area of the second air outlet of the second compartment of the cartridge is divided equally between the apertures forming the second air outlet. Providing a second compartment having a second air outlet comprising a plurality of apertures having substantially the same flow area may advantageously simplify manufacturing of the cartridge.

The second air outlet of the second compartment of the cartridge may comprise one or more apertures having any suitable cross-sectional shape. For example, the cross-sectional shape of each aperture may be circular, elliptical, square or rectangular. In embodiments in which the second air outlet of the second compartment of the cartridge comprises a plurality of apertures, advantageously each aperture has a substantially circular cross-sectional shape. In such embodiments, advantageously the diameter of each aperture is between about 0.2 millimetres and about 0.6 millimetres.

The dimensions of the one or more apertures forming the second air inlet of the second compartment of the cartridge may be the same as or different to the dimensions of the one or more apertures forming the second air outlet of the second compartment of the cartridge.

Advantageously, the dimensions of the one or more apertures forming the second air inlet of the second compartment of the cartridge may be substantially the same as the dimensions of the one or more apertures forming the second air outlet of the second compartment of the cartridge. Providing a second compartment having a second air inlet and a second air outlet comprising one or more apertures of substantially the same dimensions may advantageously simplify manufacturing of the cartridge.

Advantageously, the dimensions of the one or more apertures forming the second air outlet of the second compartment of the cartridge may be greater than the dimensions of the one or more apertures forming the second air inlet of the second compartment of the cartridge. Increasing the dimensions of the apertures forming the second air outlet of the second compartment of the cartridge relative to the dimensions of the apertures forming the second air inlet of the second compartment of the cartridge may advantageously reduce the risk of the second air outlet of the second compartment of the cartridge becoming obstructed by, for example, dust.

In embodiments in which the cartridge assembly comprises a nicotine source positioned within the first compartment and an acid source positioned within the second compartment, nicotine vapour released from the nicotine source in the first compartment of the cartridge and acid vapour released from the acid source in the second compartment of the cartridge may react with one another in the gas phase in the mouthpiece to form an aerosol of nicotine salt particles.

The cartridge assembly may comprise one or more aerosol-modifying agents positioned within the mouthpiece. For example, mouthpiece may contain one or more sorbents, one or more flavourants, one or more chemesthetic agents or a combination thereof.

The first compartment and the second compartment may be arranged symmetrically with respect to each other within the cartridge.

Advantageously, the cartridge is an elongate cartridge. In embodiments in which the cartridge is an elongate cartridge, the first compartment and the second compartment of the cartridge may be arranged symmetrically about the longitudinal axis of the cartridge.

The cartridge may have any suitable transverse cross-sectional shape. For example, the transverse cross-sectional shape of the cartridge may be circular, semi-circular, elliptical, triangular, square, rectangular or trapezoidal. Preferably, the transverse cross-sectional shape of the cartridge is square or rectangular.

The cartridge may have any suitable size.

For example, the cartridge may have a length of between about 5 millimetres and about 50 millimetres. Advantageously, the cartridge may have a length between about 10 millimetres and about 20 millimetres.

For example, the cartridge may have a width of between about 4 millimetres and about 10 millimetres and a height of between about 4 millimetres and about 10 millimetres. Advantageously, the cartridge may have a width of between about 6 millimetres and about 8 millimetres and a height of between about 6 millimetres and about 8 millimetres.

The cartridge, the cartridge cover and the mouthpiece may be formed from any suitable material or combination of materials. Suitable materials include, but are not limited to, aluminium, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibres.

The cartridge, the cartridge cover and the mouthpiece may be formed from the same or different materials.

The cartridge may be formed from one or more materials that are nicotine-resistant and acid-resistant.

The first compartment of the cartridge may be coated with one or more nicotine-resistant materials and the second compartment of the cartridge may be coated with one or more acid-resistant materials.

Examples of suitable nicotine-resistant materials and acid-resistant materials include, but are not limited to, polyethylene (PE), polypropylene (PP), polystyrene (PS), fluorinated ethylene propylene (FEP), polytetrafluoroethylene (PTFE), epoxy resins, polyurethane resins, vinyl resins and combinations thereof.

Use of one or more nicotine-resistant materials to one or both of form the cartridge and coat the interior of the first compartment of the cartridge may advantageously enhance the shelf life of the cartridge.

Use of one or more acid-resistant materials to one or both of form the cartridge and coat the interior of the second compartment of the cartridge may advantageously enhance the shelf life of the cartridge.

The cartridge assembly may comprise a heater configured to heat the at least one compartment of the cartridge. In embodiments in which the at least one compartment comprises a first compartment and a second compartment, the heater is preferably configured to heat both the first compartment and the second compartment. In such embodiments, the heater is advantageously located between the first compartment and the second compartment. That is the first compartment and the second compartment are disposed on either side of the heater.

The heater may be an electrical heater. The heater may be a resistive heater.

Advantageously, the heater is configured to heat the at least one compartment, or the first compartment and the second compartment, to a temperature of below about 250 degrees Celsius. Preferably, the heater is configured to heat the at least one compartment, or the first compartment and the second compartment, to a temperature of between about 80 degrees Celsius and about 150 degrees Celsius.

Advantageously, the heater is configured to heat the first compartment and the second compartment of the cartridge to substantially the same temperature.

As used herein with reference to the invention, by "substantially the same temperature" it is meant that the difference in temperature between the first compartment and the second compartment of the cartridge measured at corresponding locations relative to the heater is less than about 3° C.

The cartridge may comprise a heater compartment for receiving a heating element of an aerosol-generating device. In embodiments in which the at least one compartment of the cartridge comprises a first compartment and a second compartment, preferably the heater compartment is positioned between the first compartment and the second compartment. That is, the first compartment and the second compartment are disposed on either side of the heater compartment. Preferably, the cartridge cover comprises an aperture aligned with the heater compartment when the cartridge cover is in the second position. In use, a heating element of an aerosol-generating device is received within the heater compartment to heat the at least one compartment, or to heat the first compartment and the second compartment.

The cartridge may comprise a susceptor for inductively heating the at least one compartment of the cartridge. In embodiments in which the at least one compartment comprises a first compartment and the second compartment, the susceptor is advantageously located between the first compartment and the second compartment. That is, the first compartment and the second compartment are disposed on either side of the susceptor.

In use, heating the at least one compartment, or the first compartment and the second compartment, to a temperature above ambient temperature advantageously enables control of the vapour concentrations of volatile compounds stored within the at least one compartment, or the first and second compartments. For example, in embodiments in which the cartridge assembly comprises a nicotine source positioned within a first compartment and an acid source positioned within a second compartment, heating the first and second compartments enables the vapour pressure of nicotine in the first compartment and the vapour pressure of acid in the second compartment to be controlled and balanced proportionally to yield an efficient reaction stoichiometry between the nicotine and the acid. Advantageously, this may improve the efficiency of the formation of nicotine salt particles and the consistency of delivery to a user.

Advantageously, it may also reduce the delivery of unreacted nicotine and unreacted acid to a user.

The cartridge may be formed from one or more thermally conductive materials.

The first compartment of the cartridge and the second compartment of the cartridge may be coated with one or more thermally conductive materials.

Use of one or more thermally conductive materials to one or both of form the cartridge and coat the interior of the first compartment and the second compartment of the cartridge may advantageously increase heat transfer from a heater or a susceptor to the nicotine source and the acid source.

Suitable thermally conductive materials include, but are not limited to, metals such as, for example, aluminium, chromium, copper, gold, iron, nickel and silver, alloys, such as brass and steel and combinations thereof.

The cartridge may be formed of one or more materials having a low resistivity or a high resistivity depending on whether the first compartment and the second compartment are heated by conduction or induction.

The first compartment of the cartridge and the second compartment of the cartridge may be coated with one or more materials having a low resistivity or a high resistivity depending on whether the first compartment and the second compartment are heated by conduction or induction.

The cartridge may be formed by any suitable method. Suitable methods include, but are not limited to, deep drawing, injection moulding, blistering, blow forming and extrusion.

The cartridge assembly may be designed to be disposed of once the nicotine in the first compartment and the acid in the second compartment are depleted.

The cartridge may be designed to be refillable.

The cartridge assembly may simulate the shape and dimensions of a combustible smoking article, such as a cigarette, a cigar, or a cigarillo. Advantageously, in such embodiments the cartridge assembly may simulate the shape and dimensions of a cigarette.

The cartridge assembly may be configured for engagement with the housing of an aerosol-generating device. Preferably, at least one of the cartridge, the cartridge cover and the mouthpiece is configured for engagement with the housing of an aerosol-generating device.

According to a second aspect of the present invention there is provided an aerosol-generating system comprising an aerosol-generating device and a cartridge assembly according to the first aspect of the present invention, in accordance with any of the embodiments described herein. The aerosol-generating device comprises a device cavity configured to receive an upstream end of the cartridge assembly and a heater for heating the at least one compartment of the cartridge.

In those embodiments in which the cartridge comprises a heater compartment for receiving a heating element, the heater of the aerosol-generating device advantageously comprises a heating element positioned within the device cavity and configured to be received within the heater compartment of the cartridge when the upstream end of the cartridge assembly is received within the device cavity. The heating element may be a resistive heating element. In use, the heating element is received within the third compartment and heats the at least one compartment of the cartridge.

In those embodiments in which the cartridge comprises a susceptor, the heater of the aerosol-generating device advantageously comprises an inductive heater surrounding at least a portion of the device cavity. In use, the inductive heater inductively heats the susceptor, which heats the at least one compartment of the cartridge.

Advantageously, the heater of the aerosol-generating device is configured to heat the at least one compartment, or the first compartment and the second compartment, to a temperature of below about 250 degrees Celsius. Preferably, the heater of the aerosol-generating device is configured to heat the at least one compartment, or the first compartment and the second compartment, to a temperature of between about 80 degrees Celsius and about 150 degrees Celsius.

Advantageously, the heater of the aerosol-generating device is configured to heat the first compartment and the second compartment of the cartridge to substantially the same temperature.

The aerosol-generating device may further comprise a power supply for supplying power to the heater and a controller configured to control a supply of power from the power supply to the heater.

The aerosol-generating device may comprise one or more temperature sensors configured to sense the temperature of at least one of the heater and the at least one compartment. In such embodiments, the controller may be configured to control a supply of power to the heater based on a sensed temperature.

For the avoidance of doubt, features described above in relation to one aspect of the invention may also be applicable to other aspects of the invention. In particular, features described above in relation to the cartridge assembly of the invention may also relate, where appropriate, to the aerosol-generating systems of the invention, and vice versa.

Embodiments of the invention will now be described, by way of example only, with reference to the accompanying drawings, in which.

Figure 1:
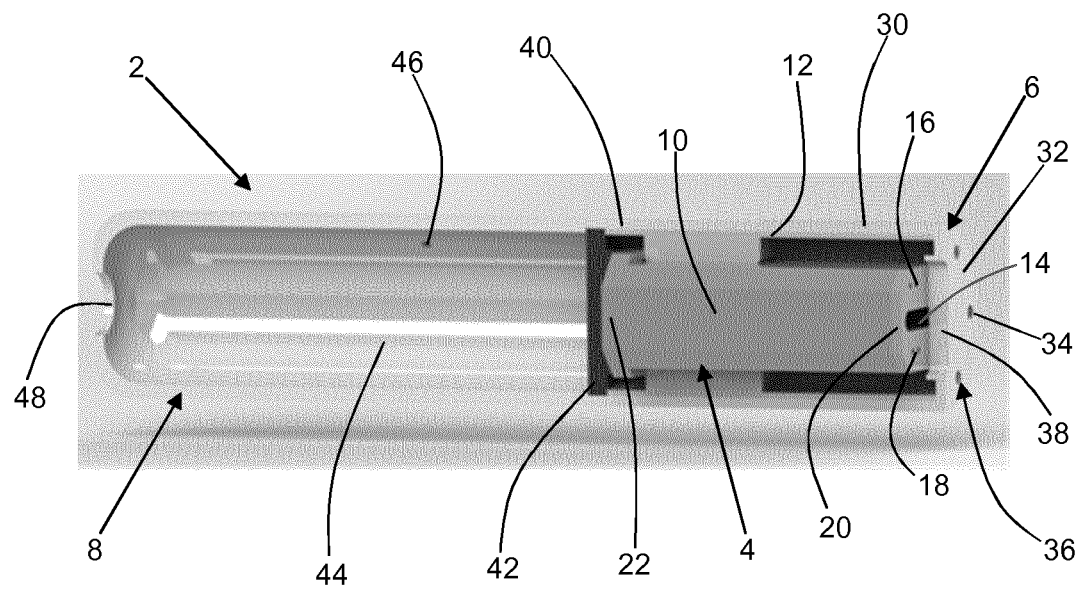
FIG. 1 shows a cross-sectional view of a cartridge assembly in accordance with a first embodiment of the present invention.

FIG. 1 shows a cartridge assembly 2 in accordance with a first embodiment of the present invention. The cartridge assembly 2 comprises a cartridge 4, a cartridge cover 6 and a mouthpiece 8.

The cartridge 4 comprises an inner housing 10 and an outer housing 12. A first compartment, a second compartment and a heater compartment 14 are positioned within the inner housing 10. A plurality of first inlet apertures form a first air inlet 16 of the first compartment and a plurality of second inlet apertures form a second air inlet 18 of the second compartment. The first air inlet 16 and the second air inlet 18 are positioned at an upstream end 20 of the inner housing 10. The first compartment comprises a first air outlet and the second compartment comprises a second air outlet, both positioned at a downstream end 22 of the inner housing 10.

A nicotine source is provided within the first compartment and an acid source is provided in the second compartment. The heater compartment 14 may be configured to receive a heating element of an aerosol-generating device. Alternatively, a susceptor may be housed in the heater compartment 14 for heating the first and second compartments via inductive heating of the susceptor using an inductive heater of an aerosol-generating device.

The outer housing 12 has a cylindrical shape and a cartridge actuation portion comprising a first helical thread formed on an outer surface of the outer housing 12.

The cartridge cover 6 comprises a cartridge cover cavity in which an upstream end of the cartridge 4 is received. A cylindrical portion 30 of the cartridge cover 6 defines an inner surface of the cartridge cover 6 on which a cartridge cover actuation portion comprising a second helical thread is formed. The second helical thread engages an upstream end of the first helical thread on the outer housing 12 of the cartridge 4.

The cartridge cover 6 further comprises a cartridge cover wall portion 32 extending across an upstream end of the cartridge cover cavity. A plurality of third inlet apertures 34 in the cartridge cover wall portion 32 form a cartridge cover air inlet 36. A heater aperture 38 is also provided in the cartridge cover wall portion 32.

As shown in FIG. 1, the cartridge cover 6 is in a first position with respect to the cartridge 4. When the cartridge cover 6 is in the first position, the cartridge cover wall portion 32 abuts the upstream end 20 of the inner housing 10 of the cartridge 4 so that the cartridge cover wall portion 32 obstructs the first air inlet 16 and the second air inlet 18.

The mouthpiece 8 comprises a mouthpiece cavity in which a downstream end of the cartridge 4 is received. A cylindrical portion 40 of the mouthpiece 8 defining the mouthpiece cavity comprises an inner surface on which a mouthpiece actuation portion comprising a third helical thread is formed. The third helical thread engages a downstream end of the first helical thread on the outer housing 12 of the cartridge 4.

The mouthpiece 8 further comprises a mouthpiece wall portion 42 extending across a downstream end of the mouthpiece cavity. A mouthpiece air inlet is provided in the mouthpiece wall portion 42. A mouthpiece chamber 44 is positioned downstream of the mouthpiece wall portion 42, the mouthpiece 8 comprising a ventilation air inlet 46 and a mouthpiece air outlet 48 in fluid communication with the mouthpiece chamber 44.

As shown in FIG. 1, the mouthpiece 8 is in a third position with respect to the cartridge 4. When the mouthpiece 8 is in the third position, the mouthpiece wall portion 42 abuts the downstream end 22 of the inner housing 10 of the cartridge 4 so that the mouthpiece wall portion 42 obstructs the first air outlet and the second air outlet.

Figure 2:
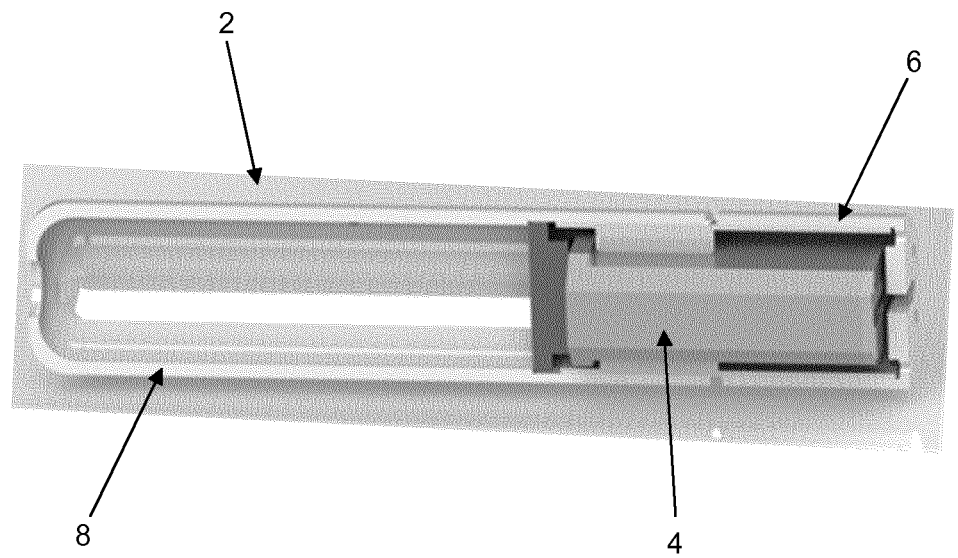
FIG. 2 shows a cross-sectional view of the cartridge assembly of FIG. 1 after the cartridge assembly has been activated.

FIG. 2 shows a cross sectional view of the cartridge assembly 2 after it has been activated. The cartridge cover 6 and the mouthpiece 8 have both been rotated through approximately 90 degrees with respect to the cartridge 4. That is, the cartridge cover 6 has been rotated from the first position shown in FIG. 1 into the second position shown in FIG. 2, and the mouthpiece 8 has been rotated from the third position shown in FIG. 1 to the fourth position shown in FIG. 2. The interaction between the first helical thread on the cartridge 4 and each of the second helical thread on the cartridge cover 6 and the third helical thread on the mouthpiece 8 has the effect of adding a translational component to the movement of each of the cartridge cover 6 and the mouthpiece 8 as each is rotated with respect to the cartridge 4. Therefore, the cartridge cover 6 exhibits a helicoidal motion with respect to the cartridge 4 when moved from the first position into the second position. The mouthpiece 8 exhibits a helicoidal motion with respect to the cartridge 4 when moved from the third position into the fourth position. The translational component of each motion results in the cartridge cover wall portion 32 and the mouthpiece wall portion 42 being spaced apart from upstream end 20 of the cartridge 4 and the downstream end 22 of the cartridge 4 respectively. Therefore, when the cartridge cover 6 and the mouthpiece 8 are in the second and fourth positions respectively, airflow paths are created through the cartridge assembly 2 from the cartridge cover air inlet 36, through the first and second compartments via the first and second air inlets 16, 18 and the first and second air outlets, through the mouthpiece air inlet, the mouthpiece chamber 44 and the mouthpiece air outlet 48. Ventilation air is also drawn into the mouthpiece chamber 44 through the ventilation air inlet 46 and out of the mouthpiece chamber 44 though the mouthpiece air outlet 48.

In use, when the cartridge assembly 2 is activated, as shown in FIG. 2, nicotine vapour is drawn into the mouthpiece chamber 44 from the first compartment of the cartridge 4 and acid vapour is drawn into the mouthpiece chamber 44 from the second compartment of the cartridge 4. The nicotine vapour and the acid vapour react in the gas phase in the mouthpiece chamber 44 to create an aerosol of nicotine salt particles for delivery to the user through the mouthpiece air outlet 48.

When the cartridge cover 6 is in the second position shown in FIG. 2, the heater aperture 38 is aligned with the heater compartment 14 so that a heater element of an aerosol-generating device may be received within the heater compartment 14.

The cartridge cover 6 and the mouthpiece 8 may be rotated back into the first and third positions respectively so that the cartridge cover wall portion 32 and the mouthpiece wall portion 42 re-obstruct the first and second air inlets 16, 18 and the first and second air outlets respectively. This may substantially prevent the loss of remaining nicotine vapour and acid vapour from the first and second compartments, respectively. The cartridge cover 6 may be moveable repeatedly between the first and second positions and the mouthpiece 8 may be moveable repeatedly between the third and fourth positions to facilitate multiple uses of the cartridge assembly 2 and to substantially prevent the loss of nicotine vapour and acid vapour from the cartridge 4 when the cartridge assembly 2 is not being used.

Figure 3:
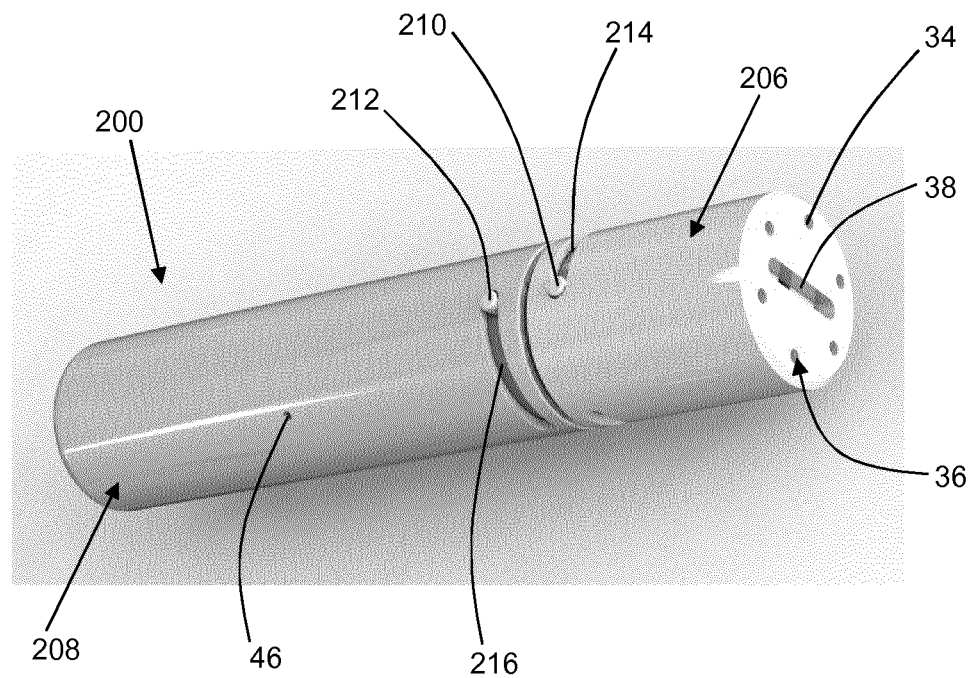
FIG. 3 shows a perspective view of a cartridge assembly in accordance with a second embodiment of the present invention.
Figure 4:
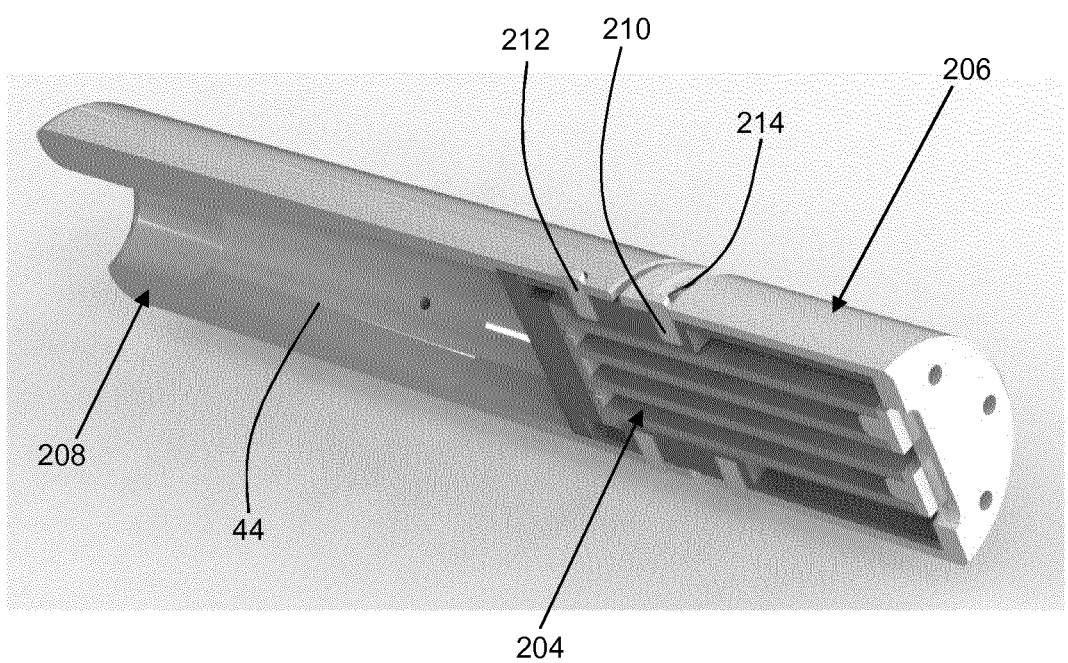
FIG. 4 shows a cross-sectional view of the cartridge assembly of FIG. 3.

FIGS. 3 and 4 show a cartridge assembly 200 in accordance with a second embodiment of the present invention. FIG. 3 shows a perspective view of the cartridge assembly 200 and FIG. 4 shows a cross-sectional view of the cartridge assembly 200. The cartridge assembly 200 is similar to the cartridge assembly 2 shown in FIGS. 1 and 2 and like reference numerals are used to designate like parts.

The cartridge assembly 200 shown in FIGS. 3 and 4 comprises a cartridge 204, a cartridge cover 206 and a mouthpiece 208. The cartridge 204, the cartridge cover 206 and the mouthpiece 208 each comprise an actuation portion to define helicoidal movement of each of the cartridge cover 206 and the mouthpiece 208 with respect to the cartridge 204. Therefore, functionally, the cartridge assembly 208 shown in FIGS. 3 and 4 is identical to the cartridge assembly 2 shown in FIGS. 1 and 2. That is, rotating the cartridge cover 206 and the mouthpiece 208 in opposite rotational directions results in helicoidal movement of the cartridge cover 206 between first and second positions with respect to the cartridge 204 and helicoidal movement of the mouthpiece 208 between third and fourth positions with respect to the cartridge 204.

However, where the cartridge, cartridge cover and mouthpiece actuation portions of the cartridge assembly 2 of FIGS. 1 and 2 each comprise a helical thread, the cartridge assembly 200 of FIGS. 3 and 4 has a different arrangement. Specifically, the cartridge 204 of the cartridge assembly 200 has first and second actuation portions comprising first and second projections 210, 212, respectively, provided on the outer surface of the cartridge 204. The cartridge cover 206 has a cartridge cover actuation portion comprising a first helical guide slot 214 formed in the cartridge cover 206, and the mouthpiece 208 has a mouthpiece actuation portion comprising a second helical guide slot 216 formed in the mouthpiece 208. The first projection 210 is engaged with the first helical guide slot 214 and the second projection 212 is engaged with the second helical guide slot 216. When the cartridge cover 206 is moved into the second position, the first projection 210 engages a first end of the first helical guide slot 214. When the cartridge cover 206 is moved into the first position, the first projection 210 engages a second end of the first helical guide slot 214. When the mouthpiece 208 is moved into the fourth position, the second projection 212 engages a first end of the second helical guide slot 216. When the mouthpiece 208 is moved into the third position, the second projection 212 engages a second end of the second helical guide slot 216.

The engagement between the first and second projections 210, 212 and the first and second helical guide slots 214, 216 has the effect of adding a translational component to the movement of each of the cartridge cover 206 and the mouthpiece 208 as each is rotated with respect to the cartridge 204. Therefore, the process of moving the cartridge cover 206 between the first and second positions and moving the mouthpiece 208 between the third and fourth positions is the same for the cartridge assembly 2 of FIGS. 1 and 2 and the cartridge assembly 200 of FIGS. 3 and 4.

The invention claimed is:

1. A cartridge assembly for an aerosol-generating system, the cartridge assembly comprising:
   a cartridge comprising:
      at least one compartment having an air inlet and an air outlet, and
      at least one cartridge actuation portion on an outer surface of the cartridge;
   a mouthpiece comprising:
      a mouthpiece cavity, wherein a downstream end of the cartridge is received within the mouthpiece cavity,
      a mouthpiece wall portion extending across a downstream end of the mouthpiece cavity, the mouthpiece wall portion comprising a mouthpiece air inlet, and
      a mouthpiece actuation portion on an inner surface of the mouthpiece cavity and engaged with the at least one cartridge actuation portion; and
   a cartridge cover comprising:
      a cartridge cover cavity, wherein an upstream end of the cartridge is received within the cartridge cover cavity,
      a cartridge cover wall portion extending across an upstream end of the cartridge cover cavity, the cartridge cover wall portion comprising a cartridge cover air inlet, and
      a cartridge cover actuation portion on an inner surface of the cartridge cover cavity and engaged with the at least one cartridge actuation portion,
   wherein the at least one cartridge actuation portion and the cartridge cover actuation portion are configured so that the cartridge cover is helicoidally moveable with respect to the cartridge from a first position in which the cartridge cover wall portion abuts an upstream end of the cartridge and obstructs the air inlet of the at least one compartment, to a second position in which the cartridge cover wall portion is spaced apart from the upstream end of the cartridge and the cartridge cover air inlet is in fluid communication with the air inlet of the at least one compartment, and wherein the at least one cartridge actuation portion and the mouthpiece actuation portion are configured so that the mouthpiece is helicoidally moveable with respect to the cartridge from a third position in which the mouthpiece wall portion abuts a downstream end of the cartridge and obstructs the air outlet of the at least one compartment, to a fourth position in which the mouthpiece wall portion is spaced apart from the downstream end of the cartridge and the mouthpiece air inlet is in fluid communication with the air outlet of the at least one compartment.

2. The cartridge assembly according to claim 1,
wherein the cartridge cover actuation portion comprises a first helical guide slot,
wherein the mouthpiece actuation portion comprises a second helical guide slot, and
wherein the at least one cartridge actuation portion comprises a first projection positioned within the first helical guide slot and a second projection positioned within the second helical guide slot.

3. The cartridge assembly according to claim 2, wherein the first projection engages a first end of the first helical guide slot when the cartridge cover is in the second position, the engagement between the first projection and the first end of the first helical guide slot prevents further helicoidal movement of the cartridge cover with respect to the cartridge in a direction away from the first position.

4. The cartridge assembly according to claim 2, wherein the second projection engages a first end of the second helical guide slot when the mouthpiece is in the fourth position, the engagement between the second projection and the first end of the second helical guide slot prevents further helicoidal movement of the mouthpiece with respect to the cartridge in a direction away from the third position.

5. The cartridge assembly according to claim 1,
wherein the at least one cartridge actuation portion comprises a first helical thread,
wherein the cartridge cover actuation portion comprises a second helical thread engaged with an upstream end of the first helical thread, and
wherein the mouthpiece actuation portion comprises a third helical thread engaged with a downstream end of the first helical thread.

6. The cartridge assembly according to claim 5,
wherein the cartridge comprises a second mechanical stop, and
wherein the first mechanical stop engages the second mechanical stop when the cartridge cover is in the second position, the engagement between the first and second mechanical stops preventing further helicoidal movement of the cartridge cover with respect to the cartridge in a direction away from the first position.

7. The cartridge assembly according to claim 5,
wherein the mouthpiece comprises a third mechanical stop,
wherein the cartridge comprises a fourth mechanical stop, and
wherein the third mechanical stop engages the fourth mechanical stop when the mouthpiece is in the fourth position, the engagement between the third and fourth mechanical stops preventing further helicoidal movement of the mouthpiece with respect to the cartridge in a direction away from the third position.

8. The cartridge assembly according to claim 1, wherein the cartridge assembly is configured to define the second position of the cartridge cover at an angular rotation with respect to the cartridge of between 70 degrees and 110 degrees from the first position.

9. The cartridge assembly according claim 1, wherein the cartridge assembly is configured to define the fourth position of the mouthpiece at an angular rotation with respect to the cartridge of between 70 degrees and 110 degrees from the third position.

10. The cartridge assembly according to claim 1, wherein each of the cartridge cover and the mouthpiece is configured for two-way helicoidal movement with respect to the cartridge so that the cartridge cover is moveable from the second position to the first position and the mouthpiece is moveable from the fourth position to the third position.

11. The cartridge assembly according to claim 1,
wherein the mouthpiece comprises a mouthpiece chamber position downstream of the mouthpiece wall portion,
wherein the mouthpiece air inlet is in fluid communication with the mouthpiece chamber, and
wherein the mouthpiece further comprises a mouthpiece air outlet at a downstream end of the mouthpiece chamber.

12. The cartridge assembly according to claim 11,
wherein the mouthpiece further comprises a ventilation air inlet providing fluid communication between the exterior of the mouthpiece and the mouthpiece chamber, and
wherein the ventilation air inlet is positioned between the mouthpiece wall portion and the downstream end of the mouthpiece chamber.

13. The cartridge assembly according to claim 1, wherein the at least one compartment comprises a first compartment having a first air inlet and a first air outlet and a second compartment having a second air inlet and a second air outlet.

14. The cartridge assembly according to claim 13,
wherein the cartridge cover air inlet comprises a third air inlet and a fourth air inlet, and
wherein the third air inlet is aligned with the first air inlet and the fourth air inlet is aligned with the second air inlet when the cartridge cover is in the second position.

15. The cartridge assembly according to claim 13, wherein the cartridge further comprises a nicotine source positioned within the first compartment and an acid source positioned within the second compartment.

16. The cartridge assembly according to claim 1,
wherein the cartridge further comprises a heater compartment configured to receive a heating element of an aerosol-generating device, and
wherein the cartridge cover comprises an aperture aligned with the heater compartment when the cartridge cover is in the second position.

17. The cartridge assembly according to claim 1, wherein the cartridge further comprises a susceptor.

18. An aerosol-generating system, comprising:
a cartridge assembly according to claim 1; and
an aerosol-generating device comprising a device cavity configured to receive an upstream end of the cartridge assembly and a heater configured to heat the at least one compartment of the cartridge of the cartridge assembly.

19. The aerosol-generating system according to claim 18, wherein the heater comprises a heating element positioned within the device cavity,
wherein the cartridge comprises a heater compartment configured to receive the heating element, and
wherein the cartridge cover comprises an aperture aligned with the heater compartment when the cartridge cover is in the second position.

20. The aerosol-generating system according to claim 18, wherein the heater comprises an inductive heater surrounding at least a portion of the device cavity, and
wherein the cartridge comprises a susceptor.

* * * * *

UNITED STATES PATENT AND TRADEMARK OFFICE
CERTIFICATE OF CORRECTION

PATENT NO. : 11,247,004 B2
APPLICATION NO. : 16/069351
DATED : February 15, 2022
INVENTOR(S) : Ali Murat Saygili It is certified that error appears in the above-identified patent and that said Letters Patent is hereby corrected as shown below:

In the Claims

In Column 21, Claim 6, after Line 51 and before Line 52, insert:
--wherein the cartridge cover comprises a first mechanical stop,--

Signed and Sealed this
Twenty-second Day of November, 2022

Katherine Kelly Vidal
*Director of the United States Patent and Trademark Office*